(12) United States Patent
Nardella

(10) Patent No.: US 6,573,292 B1
(45) Date of Patent: Jun. 3, 2003

(54) METHODS AND COMPOSITIONS FOR THE TREATMENT OF CHRONIC LYMPHOCYTIC LEUKEMIA

(75) Inventor: Francis A. Nardella, Scottsdale, AZ (US)

(73) Assignee: Salmedix, Inc., San Diego, CA (US)

( * ) Notice: Subject to any disclaimer, the term of this patent is extended or adjusted under 35 U.S.C. 154(b) by 0 days.

(21) Appl. No.: 09/720,992

(22) PCT Filed: Jul. 8, 1999

(86) PCT No.: PCT/US99/15501
§ 371 (c)(1),
(2), (4) Date: Jul. 6, 2001

(87) PCT Pub. No.: WO00/02555
PCT Pub. Date: Jan. 20, 2000

Related U.S. Application Data

(60) Provisional application No. 60/092,466, filed on Jul. 9, 1998, and provisional application No. 60/094,878, filed on Jul. 29, 1998.

(51) Int. Cl.[7] .............................................. A61K 31/40
(52) U.S. Cl. ...................................................... 514/411
(58) Field of Search ............................. 514/411, 454, 514/439

(56) References Cited

U.S. PATENT DOCUMENTS

| | | | |
|---|---|---|---|
| 4,686,213 A | 8/1987 | Ferdinandi et al. | |
| 5,561,151 A | 10/1996 | Young | 514/411 |
| 5,776,967 A | 7/1998 | Kreft et al. | |
| 5,955,504 A | 9/1999 | Wechter | 514/568 |
| 5,968,974 A | 10/1999 | Kargman et al. | 514/461 |

FOREIGN PATENT DOCUMENTS

| | | |
|---|---|---|
| WO | WO 96/28148 | 9/1996 |
| WO | WO 98/09603 | 9/1997 |
| WO | WO 97/48391 | 12/1997 |
| WO | WO 01/06990 | 2/2001 |
| WO | WO 02/12188 | 2/2002 |

OTHER PUBLICATIONS

Heath, Jr. Nonsteroidal Antiinflammatory Drugs and Human Cancer; CANCER; Nov. 15, 1994; vol. 74, No. 10, pp2885–2888.
McCracken; Antiproliferative Effects of the Enantiomers of Flurbiprofen; J Clin Pharmacol 1996: 36:540–545.
Wechter; R–Flurbiprofen Chemoprevention and Treatment of Intestinal Adenomas in the APC$^{Min}$/+ Mouse Model: Implications of Prophylaxis and Treatment of Colon Cancer;Cancer Research; 1997; 57:4316–4324.
Wechter; R–Flurbiprofen (E–7869), a chemopreventive and treatment of cancer; Inflammopharmacology; 2000; vol. 8, No. 2, pp. 189–206.
Bellosillo, et al., Aspirin and Salicylate Induce Apoptosis and Activation of Caspases in B–Cell Chronic Lymphocytic Leukemia Cells, *Blood*, 92(4):1406–1414 (1998).
Duffy, et al., Enhancement of Chemotherapeutic Drug Toxicity to Human Tumour Cells In Vitro by a Subset of Non–steroidal Anti–inflammatory Drugs (NSAIDs), *European Journal of Cancer*, 34(8), 1250–1259 (1998).
Thun, Aspirin NSAIDs, and Digestive Tract Cancers, *Cancer and Metastasis Reviews*, 13: 269–277 (1994).
Wechter, Rac–Flurbiprofen Is More Ulcerogenic Than Its (S)–Enantiomer, *Chirality* 5: 492–494 (1993).

*Primary Examiner*—Jerome D Goldberg
(74) *Attorney, Agent, or Firm*—Suzanne L. Biggs, Esq.; Pillsbury Winthrop LLP

(57) ABSTRACT

Methods for the treatment of Chronic Lymphocytic Leukemia and B-cell and T-cell lymphomas are provided. These methods comprise administering to a patient in need of treatment an effective amount of certain indole and carbazole compounds, such as etodolac.

14 Claims, 2 Drawing Sheets

METHODS AND COMPOSITIONS FOR THE TREATMENT OF CHRONIC LYMPHOCYTIC LEUKEMIA

This is a 371 of PCT/US99/15501 filed Jul. 8, 1999. This application also claims the benefit of provisional application Nos. 60/092,466 filed Jul. 9, 1998 and 60/094,878 filed Jul. 29, 1998.

FIELD OF THE INVENTION

The present invention relates to the use of indole derivatives characterized by having a 1,3,4,9-tetrahydropyrano [3,4-b]indole, 1,3,4,9-tetrahydrothiopyrano [3,4-b]indole, 1,2,3,4-tetrahydro-4H carbazole or 2,3,4,9-tetrahydro-1H-carbazole nucleus, such as etodolac, in the treatment of chronic lymphocytic leukemia, and B-cell and T-cell lymphomas.

BACKGROUND OF THE INVENTION

Chronic lymphocytic leukemia (CLL) is a heterogeneous group of diseases characterized by different maturation states of the B-cells and T-cells, which are related to the aggressiveness of the disorder. Accordingly, CLL is commonly classified into separate categories, including B-cell chronic lymphocytic leukemia of classical and mixed-types, B-cell and T-cell prolymphocytic leukemia, hairy-cell leukemia and hairy-cell variant, splenic lymphoma with circulating villous lymphocytes, large granular lymphocytic leukemia, adult T-cell leukemia/lymphoma syndrome and leukemic phases of malignant lymphomas of both B-cell and T-cell types.

B-cell chronic lymphocytic leukemia (B-CLL) is characterized by proliferation and accumulation of B-lymphocytes that appear morphologically mature but are biologically immature. B-CLL typically occurs in persons over 50 years of age. This disorder accounts for 30% of leukemias in Western countries, with 10,000 new cases being diagnosed annually in the United States alone. The disorder is characterized by proliferation of biologically immature lymphocytes (lymphocytosis), which typically express low levels of surface immunoglobulins, which upon organ infiltration cause lymph-node enlargement and hepato-splenomegaly. In the advanced stages of the disease, bone marrow occupation by the abnormal lymphocytes causes bone marrow failure, resulting in anemia and thrombocytopenia.

The B-cells in CLL have receptors for mouse erythrocytes, a marker of immature B-cells. An increased number of T-cells has been reported in this disorder with an increase in the number of T-suppressor cells. Typically, an inversion of the T-helper/suppressor ratio results, with increased suppressor T-cells and decreased helper T-cells. The absolute number of natural killer cells may also be increased. In addition, chromosome analysis provides prognostic information about overall survival, in addition to that supplied by clinical data in patients with B-cell CLL.

It has been suggested that certain non-steroidal anti-inflammatory drugs (NSAIDs) may exhibit chemopreventative and anti-neoplastic properties. For example, Piazza et al., *Cancer Research* 57:2452–2459 (1997), discloses that sulindac (an NSAID that acts as a cyclooxygenase inhibitor) causes regression of and prevents recurrence of colonic adenomas in patients with familial adenomatous polyposis in a manner that appears to be independent of the drug's cyclooxygenase inhibition activity. Although induction of apoptosis was suggested, the actual mechanism of action of this NSAID in the inhibition of cell growth is poorly understood.

The compound etodolac, 1,8-diethyl-1,3,4,9-tetrahydro[3,4-b]-indole-1-acetic acid, falls generally in the class of NSAIDs and is a cyclooxygenase inhibitor. Etodolac is used to treat mild-to-moderate pain, osteoarthritis, and rheumatoid arthritis. Other related indole compounds have also been shown to exhibit similar activity. For example, U.S. Pat. Nos. 3,843,681, 3,939,178, 3,974,179 and 4,686,213 disclose indole derivatives based on the 1,3,4,9-tetrahydropyrano[3,4-b]-indole-1-acetic acid nucleus that are stated to exhibit anti-inflammatory, analgesic, antibacterial and/or antifingal activity. Similar 1,2,3,4-tetrahydro-4H-carbazole and 2,3,4,9-1H-carbazole compounds and their use as cyclooxygenase-2 (COX-2) inhibitors for antiarthritic, colorectacl cancer and Alzheimer's therapy are also disclosed in U.S. Pat. Nos., 5,776,967, 5,824,699 and 5,830,911.

SUMMARY OF THE INVENTION

It has now been surprisingly discovered that the number of circulating leukemic lymphocytes in patients suffering from chronic lymphocytic leukemia (CLL), such as B-cell CLL, is reduced by the administration of certain indole compounds, such as the nonsteroidal anti-inflammatory drug etodolac or related indole compounds, in vivo, in vitro, and in situ.

Thus, in one aspect the present invention relates to the discovery that etodolac or related indole compounds reduce the level of leukemic lymphocytes in patients with CLL.

The present invention also relates to the use of etodolac, related indole compounds and/or salts or functional derivatives thereof, in the manufacture of a pharmaceutical composition for the treatment of CLL or B-cell lymphomas.

In yet another aspect, the invention relates to pharmaceutical compositions for the treatment of CLL or B-cell lymphomas, comprising etodolac, related indole compounds and/or salts thereof, as active ingredients, optionally together with pharmaceutically acceptable carriers and/or excipients and/or adjuvants.

It is contemplated that effective indole compounds of this invention are characterized by having a pyrano [3,4-b] indole, thiopyrano [3,4-b]indole or carbazole nucleus bearing a substituent at position 1, said substituent incorporating an acid, ester or amide function therein. These derivatives may be represented by Formula I:

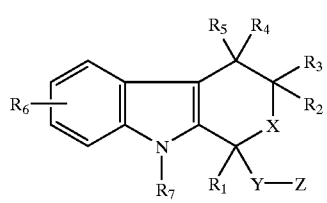

Formula I in which $R_1$ is selected from the group consisting of hydrogen, lower alkyl, lower alkenyl, lower alkynyl, alkoxyloweralkyl, lower cycloalkyl, phenyl, benzyl and 2-thienyl; $R_2$ and $R_3$ are the same or different and are each selected from the group consisting of hydrogen and lower alkyl; $R_4$ and $R_5$ are the same or different and are each selected from the group consisting of hydrogen, lower alkyl, —$NH_2$, —NHCHO, —$NHCONH_2$, =NW, oxo, —OH and —$OCH_3$, wherein W is hydroxy, alkoxy, aryloxy, carboxyalkyloxy, arylamino or alkylsulfonylamino; $R_6$ is selected from the group consisting of hydrogen, lower alkyl, lower alkenyl, lower alkynyl, trifluoromethyl, hydroxy, lower alkoxy, trifluoroloweralkoxy, benzyloxy, araloxy, lower alkanoyloxy, acyl, amino, nitro, cyano, alkylimido, halo, mercapto, loweralkylthio, alkylsulfinyl, alkylsulfonyl, alkylsulfonamido and sulfamoyl; $R_7$ is selected from the group consisting of hydrogen, lower alkyl and lower alkenyl; X is selected from the group consisting of carbon, oxy and thio; Y is selected from the group consisting of carbonyl,

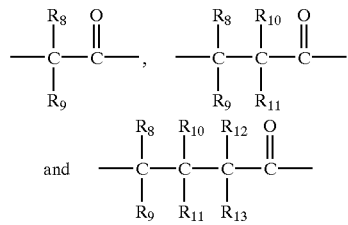

in which each of $R_8$, $R_9$, $R_{10}$, $R_{11}$, $R_{12}$ and $R_{13}$ is hydrogen or lower alkyl; and Z is selected from the group consisting of hydroxy, lower alkoxy, amino, lower alkylamino, di(lower)alkylamino and phenylamino.

Also included within the scope of this invention are pyrano [3,4-b]indole and thiopyrano [3,4-b]indole derivatives of Formula I in which $R_6$ represents from one to four substituents, which may be present simultaneously, at positions 5, 6, 7 and 8 thereof. The exact nature of such substituents does not have to be limited necessarily by the above definitions of $R_6$, and $R_6$ may also include additional substituents, for example, mercapto, lower alkylthio, trifluoromethyl and other halo(lower)alkyls, amino and sulfamoyl, provided that any two such substituents do not interfere with each others presence. Accordingly the indole derivatives of this invention are represented also by general Formula Ia:

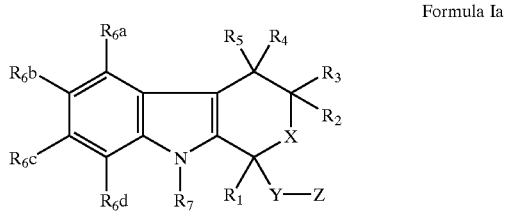

Formula Ia in which $R_1$, $R_2$, $R_3$, $R_4$, $R_5$, $R_7$, X, Y and Z are as defined above and $R_{6a}$, $R_{6b}$, $R_{6c}$ and $R_{6d}$ are the same or different and each is selected from the group consisting of hydrogen, lower alkyl, lower alkenyl, lower alkynyl, trifluoromethyl, hydroxy, lower alkoxy, trifluoroloweralkoxy, benzyloxy, araloxy, lower alkanoyloxy, acyl, amino, nitro, cyano, alkylimido, halo, mercapto, loweralkylthio, alkylsulfinyl, alkylsulfonyl, alkylsulfonamido and sulfamoyl.

In yet other aspects of the invention, methods are provided for the treatment of CLL and other lymphomas by administering to a patient in need thereof, a lymphocyte reducing amount of a compound of Formula I or Ia, either alone or together with a pharmaceutically acceptable carrier.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
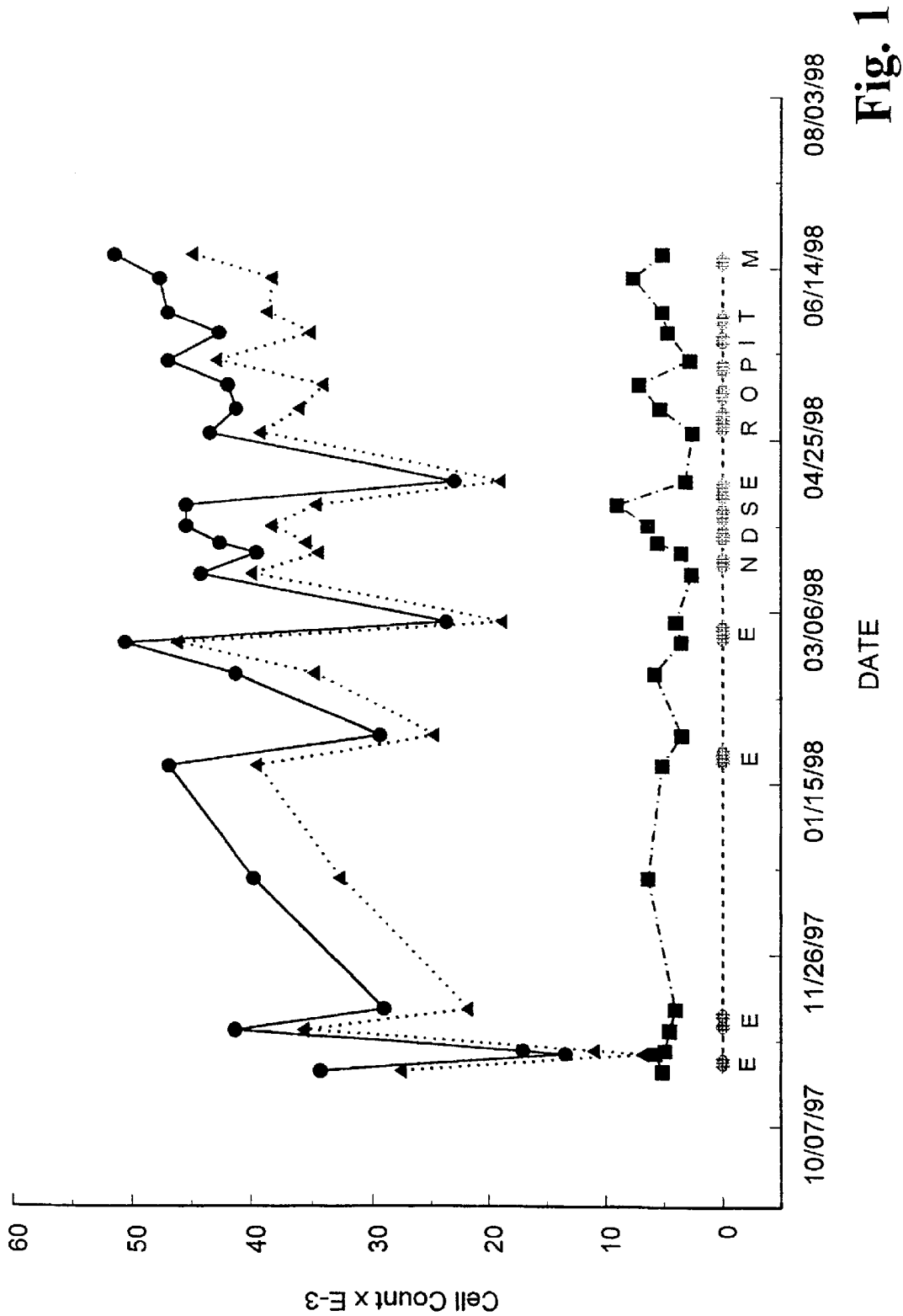
FIG. 1 is a graphical representation of the white blood cell count (WBC, solid circles), lymphocyte count (LYC, solid triangles) and neutrophil count (NC, solid squares) over time after administration of various nonsteroidal anti-inflammatory drugs (NSAIDs) to a patient suffering from CLL at the times shown as solid diamonds, as described in Example 1. The administered NSAIDs were etodolac (E, 300 mg, bidx3–6 days), naproxen (N, 250 mg, tidx4 days), diclofenac (D, 50 mg tidx4 days), sulindac (S, 200 mg, bidx4 days), nabumetone (R, 500 mg, bidx6 days), oxaprozin (O, 600 mg, bidx4 days), prioxicam (P, 20 mg, qdx3 days), indomethacin (I, 25 mg tidx3 days), tolmetin (T, 400 mg bidx3 days) and ibuprofen (M, 400 mg tidx3 days). The dose and duration for administration is shown in FIG. 1.

In accordance with the present invention, a method is provided for the prophylaxix or treatment of chronic lymphocytic leukemia (CLL) in a patient, comprising administering to said patient a therapeutically effective amount of an indole derivative of the formula:

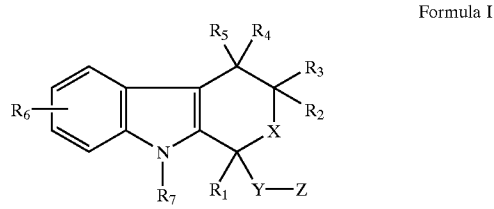

Formula I in which $R_1$ is selected from the group consisting of hydrogen, lower alkyl, lower alkenyl, lower alkynyl, alkoxyloweralkyl, lower cycloalkyl, phenyl, benzyl and 2-thienyl; $R_2$ and $R_3$ are the same or different and are each selected from the group consisting of hydrogen and lower alkyl; $R_4$ and $R_5$ are the same or different and are each selected from the group consisting of hydrogen, lower alkyl, —$NH_2$, —NHCHO, —$NHCONH_2$, =NW, oxo, —OH and —$OCH_3$, wherein W is hydroxy, alkoxy, aryloxy, carboxyalkyloxy, arylamino or alkylsulfonylamino; $R_6$ is selected from the group consisting of hydrogen, lower alkyl, lower alkenyl, lower alkynyl, trifluoromethyl, hydroxy, lower alkoxy, trifluoroloweralkoxy, benzyloxy, araloxy, lower alkanoyloxy, acyl, amino, nitro, cyano, alkylimido, halo, mercapto, loweralkylthio, alkylsulfinyl, alkylsulfonyl, alkylsulfonamido and sulfamoyl; $R_7$ is selected from the group consisting of hydrogen, lower alkyl and lower alkenyl; X is selected from the group consisting of carbon, oxy and thio; Y is selected from the group consisting of carbonyl,

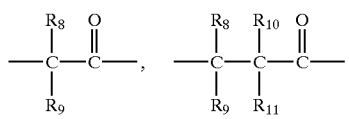

-continued and 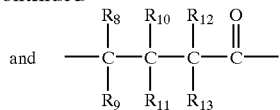

in which each of $R_8$, $R_9$, $R_{10}$, $R_{11}$, $R_{12}$ and $R_{13}$ is hydrogen or lower alkyl; and Z is selected from the group consisting of hydroxy, lower alkoxy, amino, lower alkylamino, di(lower)alkylamino and phenylamino, or a pharmaceutically acceptable salt thereof.

Also included within the scope of this invention are pyrano [3,4-b]indole and thiopyrano [3,4-b]indole derivatives of Formula I in which $R_6$ represents from one to four substituents, which may be present simultaneously, at positions 5, 6, 7 and 8 thereof. The exact nature of such substituents does not have to be limited necessarily by the above definitions of $R_6$, and $R_6$ may also include additional substituents, for example, mercapto, lower alkylthio, trifluoromethyl and other halo(lower)alkyls, amino and sulfamoyl, provided that any two such substituents do not interfere with each others presence. Accordingly the indole derivatives of this invention are represented also by general Formula Ia:

Formula Ia

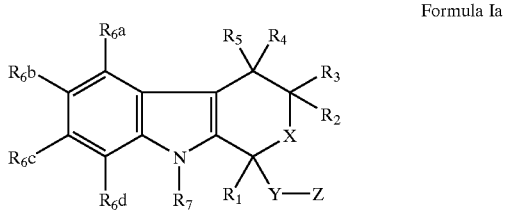

in which $R_1$, $R_2$, $R_3$, $R_4$, $R_5$, $R_7$, X, Y and Z are as defined above and $R_{6a}$, $R_{6b}$, $R_{6c}$ and $R_{6d}$ are the same or different and each is selected from the group consisting of hydrogen, lower alkyl, lower alkenyl, lower alkynyl, trifluoromethyl, hydroxy, lower alkoxy, trifluoroloweralkoxy, benzyloxy, araloxy, lower alkanoyloxy, acyl, amino, nitro, cyano, alkylimido, halo, mercapto, loweralkylthio, alkylsulfinyl, alkylsulfonyl, alkylsulfonamido and sulfamoyl, or a pharmaceutically acceptable salt thereof.

The preparation of compounds of Formulas 1 and 1a is disclosed in U.S. Pat. Nos. 3,843,681, 3,939,178, 3,974,179, 4,686,213, 4,748,252, 5,776,967, 5,824,699 and 5,830,911 the disclosures of which are incorporated herein by reference.

In a presently preferred embodiment of the invention, the indole compound of Formula I is etodolac, having the formula

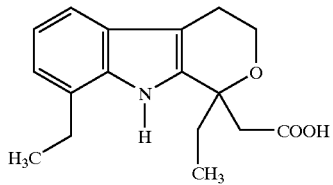

or a pharmaceutically acceptable salt thereof. Methods for the synthesis of etodolac are disclosed in U.S. Pat. Nos. 4,585,877 and 5,599,946, which are incorporated herein by reference. Etodolac is commercially available under the tradename Lodine®, Wyeth-Ayerst Laboratories Division of American Home Products Corporation, Philadelphia, Penn., U.S.A. Also included within the scope of this invention are the isomers of the compounds of Formula I resulting from the asymmetric centers contained therein. The commercially available etodolac product is a racemic mixture. U.S. Pat. No. 5,561,151 discloses the resolution of a mixture of the enantiomers of etodolac using conventional means, and the use of the separated R(−) isomer as an analgesic. Thus, it is further contemplated that the (R)- and (S)-isomers of etodolac may be separated, and used separately in the practice of the invention.

As used herein in connection with the indole derivatives of the invention, the term "lower alkyl" contemplates both straight and branched chain alkyl radicals containing from one to six carbon atoms and includes methyl, ethyl, propyl, isopropyl, butyl, isobutyl, 2-methylpentyl and the like.

As used herein, the term "lower alkenyl" contemplates both straight and branched chain alkenyl radicals containing from two to six carbon atoms and includes vinyl, allyl, 1-propenyl, methallyl, 2-ethyl-3-butenyl and the like.

As used herein, the term "lower alkynyl" contemplates both straight and branched chain alkynyl radicals containing from two to six carbon atoms and includes ethynyl, propargyl, 1,1-dimethylpropargyl and the like.

As used herein, the term "lower cycloalkyl" contemplates saturated cyclic hydrocarbon radicals containing from three to six carbon atoms and includes cyclopropyl, cyclobutyl, cyclopentyl and the like.

As used herein, the term "lower alkoxy" contemplates both straight and branched chain alkoxy radicals containing from one to four carbon atoms and includes methoxy, ethoxy, isopropoxy and the like.

As used herein, the term "lower alkanoyloxy" contemplates both straight and branched chain alkanoyloxy radicals containing from two to six carbon atoms and includes acetoxy, propionyloxy, hexanoyloxy and the like.

As used herein, the term "acyl" refers to the divalent group —C(O)—.

The term "aryl" as used herein refers to cyclic aromatic hydrocarbon chains having twenty or fewer carbon atoms, e.g., phenyl, naphthyl, biphenyl and anthracenyl. One or more carbon atoms of the aryl group may also be substituted with, e.g.: alkyl; aryl; heterocycle; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The terms "aralkyl" or "aralkoxy" as used herein refers to an aryl group that is joined to a parent structure by an alkyl or alkoxy group as described above, e.g., benzyl, α-methylbenzyl, phenethyl, and the like.

As used herein, the term "halo" contemplates halogens and includes fluorine, chlorine, bromine and iodine.

Where the term "lower" is used herein as part of the description of alkylamino and dialkylamino, it contemplates one to six carbon atoms of each alkyl group of such a radical and includes a methylamino, n-hexylamino, dimethylamino, diethylamino and the like.

When the present indole derivatives of this invention are employed in accordance with the invention in warm-blooded animals, e.g., mice, rats, or humans, they may be administered orally, alone or in dosage forms, i.e., capsules or tablets, combined with pharmacologically acceptable carriers or excipients, such as starch, milk sugar and so forth. They may also be administered orally in the form of solutions in suitable vehicles such as vegetable oils, or they may be injected parenterally. For parenteral administration they may be used in the form of a sterile solution containing other solutes, for example, enough saline or glucose to make the solution isotonic.

The dosage of the indole derivatives of this invention will vary with the particular compound chosen and form of administration. Furthermore, it will vary with the particular host under treatment. The proportion of the compound is determined by the solubility and chemical nature of the compound, chosen route of administration and standard biological practice. Generally, the compounds of this invention are administered at a concentration level that affords the benefits of the invention without any deleterious side effects. Effective concentration levels are usually obtained within a therapeutic range of 1.0 mg to 500 mg of an indole compound of the invention per kg of body weight of the patient per day, with a preferred range of 10 to 100 mg/kg per day.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, sulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid. maleic acid, succinic acid and citric acid. Basic addition-salts can be prepared in silu during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Pharmaceutical compositions comprising at least one indole or carbazole compound of Formula I or Formula Ia, may also include suitable solutions for administration intravenously, subcutaneously, dermally, orally, mucosally or rectally and may be administered by injection or orally, and contain from about 0.01 to 99 percent, preferably from about 20 to 75 percent of active component together with the excipient. Pharmaceutical compositions for oral administration include tablets and capsules. Compositions which can be administered rectally include suppositories. Pharmaceutical compositions according to the invention may be administered via the conventional ways of administration. Preferred ways of administration are oral, intravenous, intramuscular or subcutaneous. The pharmaceutical compositions may also be administered continuously, i.e., by way of infusion. The formulation and dose will depend on the condition to be treated, the route of administration and the condition and the body weight of the patient to be treated. The exact dose will be determined by the attending physician.

The pharmaceutical compositions according to the invention are prepared in the usual manner, for example by mixing the active ingredient with pharmaceutically and physiologically acceptable carriers and/or stabilizers and/or excipients, as the case may be, and are prepared in dosage form, e.g., by lyophilization in dosage vials. As used herein, the term "pharmaceutically acceptable" refers to a carrier medium which does not interfere with the effectiveness of the biological activity of the active ingredients and which is not toxic to the hosts to which it is administered.

The composition used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., REMINGTON'S PHARMACEUTICAL SCIENCES, Mack Publishing Co.: Easton, Pa., 17th Ed. (1985). Preferably, administration will be by oral or parenteral (including subcutaneous, intramuscular, intravenous, and intradermal) routes. More preferably, the route of administration will be oral. The therapeutic methods and agents of this invention can of course be used concomitantly or in combination with other methods and agents for treating CLL.

While it is possible to administer the active ingredient of this invention alone, it is preferable to present a therapeutic agent as part of a pharmaceutical formulation or composition. The formulations of the present invention comprise at least one compound of this invention in a therapeutically or pharmaceutically effective dose together with one or more pharmaceutically or therapeutically acceptable carriers and optionally other therapeutic ingredients. Various considerations for preparing such formulations are described, e.g., in Gilman et al. (eds.) GOODMAN AND GILMAN'S: THE PHARMACOLOGICAL BASES OF THERAPEUTICS, 8th Ed., Pergamon Press (1990); and REMINGTON'S supra, each of which is incorporated herein by reference for all purposes. Methods for administration are discussed therein, e.g., for oral, intravenous, intraperitoneal, intramuscular, and other forms of administration. Typically, methods for administering pharmaceutical compositions will be either topical, parenteral, or oral administration methods for prophylactic and/or therapeutic treatment. Oral administration is preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013; 4,460,562; 4,466,953; 4,482,534; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases such as skin cancer and fungal infections of the skin (pathogenic fungi typically express telomerase activity).

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a telomerase inhibitor of the invention would be enhanced, one can select a composition for delivery to a mucosal membrane, e.g., in cases of colon cancer one can use a suppository to deliver the telomerase inhibitor.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a premanufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol, or the like. These compositions will be sterilized by conventional, well known sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolamine oleate, etc. Such formulations will be useful in treating ovarian cancers.

Another method of parenteral administration employs the implantation of a slow-release or sustained-release system, such that a constant level of dosage is maintained. See, e.g., U.S. Pat. No. 3,710,795, incorporated herein by reference.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art; for example, see REMINGTON'S PHARMACEUTICAL SCIENCES, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds of the invention can be administered for prophylactic and/or therapeutic treatments. In therapeutic applications, compositions are administered to a patient already suffering from CLL, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In addition to internal (in vivo) administration, the compounds and compositions of the invention may be applied ex vivo to achieve therapeutic effects. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agent for longer periods or at higher concentrations than otherwise available.

Once improvement of the patient's conditions has occurred, a maintenance dose is administered if necessary. Subsequently, the dosage or the frequency of administration, or both. can be reduced. as a function of the systems. to a level at which the improved condition is retained. When the symptoms have been alleviated to the desired level, treatment can cease. Patients can, however, require additional treatment upon any recurrence of the disease symptoms.

In prophylactic applications (e.g. chemoprevention), compositions containing the compounds of the invention are administered to a patient susceptible to or otherwise at risk of a CLL. Such an amount is defined to be a "prophylactically effective amount or dose." In this use, the precise amounts again depend on the patient's state of health and weight.

EXAMPLE 1

In Vivo Administration

A patient was confirmed to have B-cell CLL by lymphocyte typing and bone marrow studies. The patient was staged at 0 by the Rai classification system. The patient's lymphcyte phenotype, CD5+, CD19+, CD20+, CD25+ and FMC7+. On Oct. 23, 1997, the patient's white blood cell count was 34.3×E3 and the lymphocyte count was 27.44×E3. On Oct. 25, 1997 through Oct. 27, 1997, the patient was administered 300 mg of etodolac BID for neck pain. On Oct. 28, 1997, the patient developed petechiae (bleeding from the capillaries) on the shins. A complete blood count revealed that the patient's platelet count was normal, but that both the white blood cell count (13.40×E3) and the lymphocyte count (6.70×E3) were significantly reduced, as shown in FIG. 1.

Figure 2:
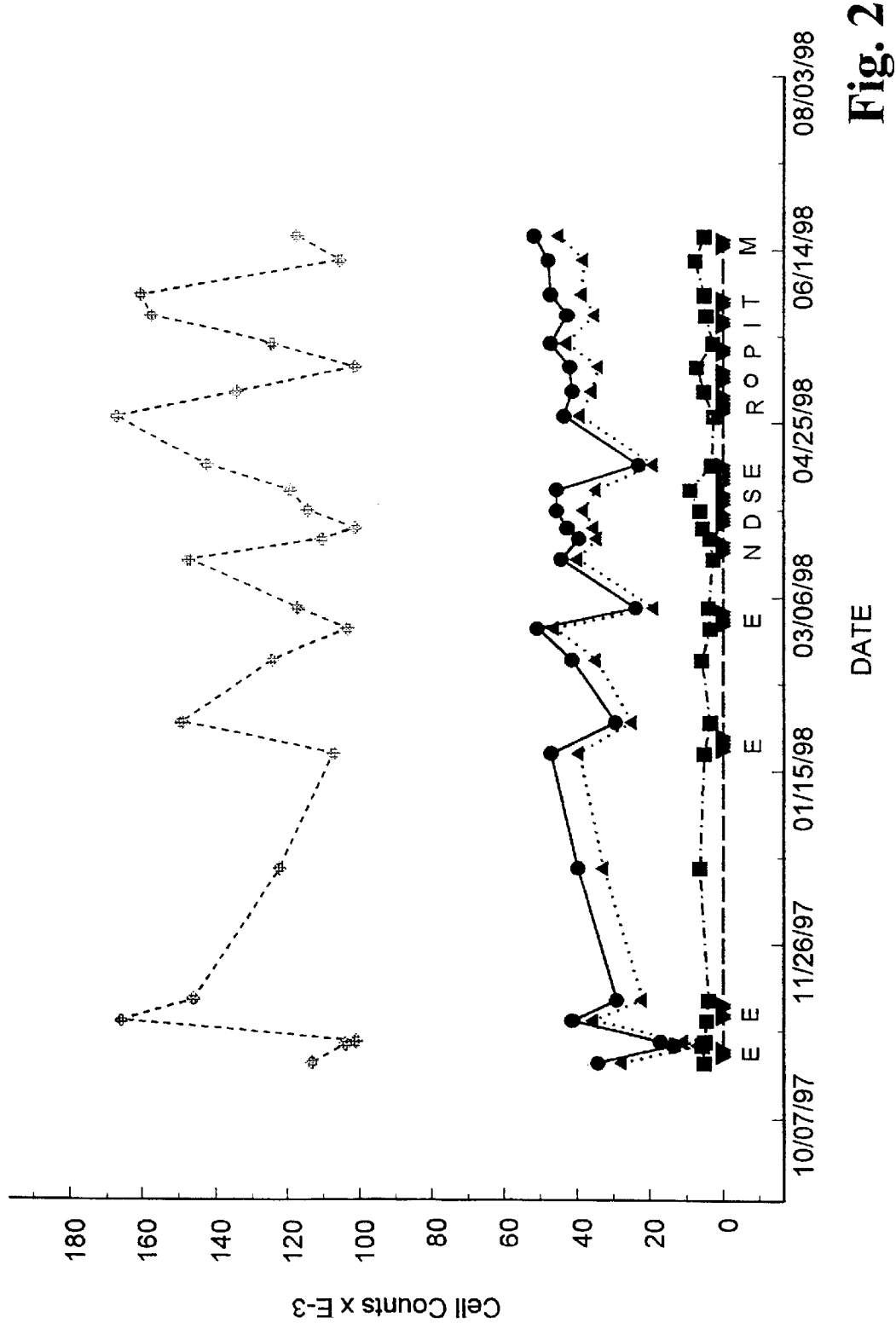
FIG. 2 is a graphical representation of the white blood cell count (WBC, solid circles), lymphocyte count (LYC, solid triangles) and neutrophil count (NC, solid squares) over time after administration of the non-steroidal anti-inflammatory drugs (NSAIDs) described in FIG. 1 to a patient suffering with CLL at the times shown as inverted triangles, as shown in FIG. 1, with the addition of the platelet count (PLTCT, solid diamonds) of the patient.

Subsequently, etodolac was administered to the patient at a dose of 300 mg BID for the periods Nov. 5, 1997–Nov. 9, 1997, Jan. 21, 1998–Jan. 25, 1998, Feb. 26, 1998–Mar. 2, 1998 and Apr. 8, 1998–Apr. 13, 1998. The results are shown in FIGS. 1 and 2, with the effect on platelet count also being shown in FIG. 2, and are compared with the results of administration to the same patient during intervening periods of the NSAIDs naproxen (N), diclofenac (D), sulindac (S), nabumetone (R), oxaprozin (O), piroxicam (P), indomethacin (I), tolmetin (T) and ibuprofen (M). The results from the etodolac administration are averaged and compared with the data for naproxin, diclofenac, sulindac, nabumetone, oxaprozin, piroxicam, indomethacin, tolmetin and ibuprofen in the following Table 1.

TABLE 1

| Treatment | WBC Count × E-3 | Lymphocyte Ct. × E-3 | Neutrophil Count × E-3 | Platelet Count × E-3 |
|---|---|---|---|---|
| Baseline* | 47.52 +/− 2.68 | 39.90 +/− 5.79 | 6.64 +/− 2.07 | 110 +/− 8.33 |
| Etodolac* | 25.27 +/− 3.51 | 20.68 +/− 3.41 | 3.58 +/− 0.40 | 136 +/− 16.8 |
|  | $p < 0.001$ | $p < 0.001$ | $p < 0.05$ | $p < 0.001$ |
| Baseline | 44.1 | 39.69 | 2.65 | 147 |
| Naproxen | 39.4 | 34.28 | 3.55 | 110 |
| Baseline | 42.5 | 35.26 | 5.53 | 101 |
| Diclofenac | 45.3 | 38.05 | 6.34 | 114 |
| Baseline | 45.3 | 38.05 | 6.34 | 114 |
| Sulindac | 45.3 | 34.43 | 9.01 | 119 |
| Baseline | 43.3 | 38.97 | 2.60 | 167 |
| Nabumetone | 41.1 | 35.76 | 5.34 | 134 |
| Baseline | 41.1 | 35.76 | 5.34 | 134 |
| Oxaprozin | 41.8 | 33.86 | 7.12 | 101 |
| Baseline | 41.8 | 33.86 | 7.12 | 101 |
| Piroxicam | 46.8 | 42.59 | 2.81 | 124 |
| Baseline | 46.8 | 42.59 | 2.81 | 124 |
| Indomethacin | 42.5 | 34.85 | 4.68 | 157 |
| Baseline | 42.5 | 34.85 | 4.68 | 157 |
| Tolmetin | 46.8 | 38.38 | 5.15 | 160 |
| Baseline | 47.5 | 38.00 | 7.60 | 105 |
| Ibuprofen | 51.3 | 44.63 | 5.13 | 117 |

*Means +/− SD of 3 experiments

As is readily apparent from the foregoing, etodolac treatment resulted in substantial reductions of the white blood cell count and lymphocyte count of the patient, while treatment with the NSAIDs naproxen, dicifenac, sulindac, nabumetone, oxaprozin, piroxicam, indomethacin, tolmetin and ibuprofen exhibited relatively little impact on these factors. The platelet count also increased significantly with etodolac.

To examine the possibility that a metabolite of etodolac or a serum factor may be necessary to achieve the clinical effect, the in vivo percentages of viable, apoptotic and late apoptotic or necrotic cells of isolated mononuclear cells were measured by flow cytometry using FITC annexin and propridium iodide assay. During early apoptosis and preceding DNA fragmentation, phosphatydylserine becomes exposed and bond by annexin V. Later in apoptosis and in cell necrosis, cells also become permeable to propidium iodide. FITC labeled annexin B and propidium iodide are easily detected by flow cytometry. Mononuclear cells were isolated from the peripheral blood of the patient by differential centrifugation on ficoll-Hypaque at baseline and then daily for three additional days after administration of etodolac. As the lymphocyte count dropped after administration of etodolac, the percentage of apoptotic cells remained the same. However, the percentage of viable cells increased and the percentage of late apoptotic or necrotic cells decreased. This result suggests that etodolac does not achieve the reduction of lymphocytes by direct killing, but likely increases the clearance of leukemic cells either into the phagocytic system or diverts them to various tissue compartments. To examine the possibility that etodolac might enhance the clearance of leukemic lymphocytes by enhancing phagocytosis by macrophages, TAMRA stained isolated mononuclear cells from the patient were incubated with normal human adherent mononuclear cells in the presence of naproxen or etodolac in vitro. After an overnight incubation, the adherent cells were isolated and analyzed by flow cytometry for uptake of TAMRA stained cells from the patient. No increase in the uptake of the stained leukemic mononuclear cells by the normal adherent cells could be detected for etodolac compared to naproxen. To test the possibility that a metabolite of etodolac could be responsible for the effect, serum from the patient was collected free of drug, after receiving naproxen 375 mg bid for two days and after receiving etodolac 400 mg bid for two days, and tested in the above manner. No enhancement of phagocytosis of lymphocytes with etodolac serum was apparent. Although not wishing to be bound by any particular theory, these data suggest that etodolac achieves its effect most likely by a novel mechanism of changing the compartmentalization of B cell CLL leukemic lymphocytes.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for the treatment of chronic lymphocytic leukemia (CLL) in a patient, comprising administering to said patient a therapeutically effective amount of an indole or carbazole derivative of the formula:

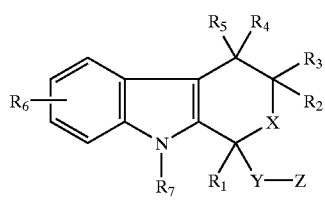

Formula I in which $R_1$ is selected from the group consisting of hydrogen, lower alkyl, lower alkenyl, lower alkynyl, alkoxyloweralkyl, lower cycloalkyl, phenyl, benzyl and 2-thienyl; $R_2$ and $R_3$ are the same or different and are each selected from the group consisting of hydrogen and lower alkyl; $R_4$ and $R_5$ are the same or different and are each selected from the group consisting of hydrogen, lower alkyl, —$NH_2$, —NHCHO, —$NHCONH_2$, =NW, oxo, —OH and —$OCH_3$, wherein w is hydroxy, alkoxy, aryloxy, carboxyalkyloxy, arylamino or alkylsulfonylamino; $R_6$ is selected from the group consisting of hydrogen, lower alkyl, lower alkenyl, lower alkynyl, trifluoromethyl, hydroxy, lower alkoxy, trifluoroloweralkoxy, benzyloxy, araloxy, lower alkanoyloxy, acyl, amino, nitro, cyano, alkylimido, halo, mercapto, loweralkylthio, alkylsulfinyl, alkylsulfonyl, alkylsulfonamido and sulfamoyl; $R_7$ is selected from the group consisting of hydrogen, lower alkyl and lower alkenyl; X is selected from the group consisting of carbon, oxy and thio; Y is selected from the group consisting of carbonyl,

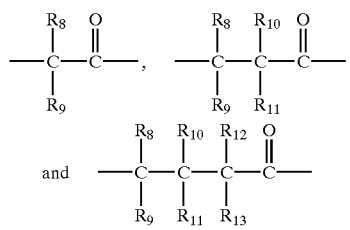

in which each of $R_8$, $R_9$, $R_{10}$, $R_{11}$, $R_{12}$ and $R_{13}$ is hydrogen or lower alkyl; and Z is selected from the group consisting of hydroxy, lower alkoxy, amino, lower alkylamino, di(lower)alkylamino and phenylamino, or a pharmaceutically acceptable salt thereof.

2. The method of claim 1 wherein the indole or carbazole derivative is etodolac.

3. The method of claim 2 wherein about 1.0 mg to 500 mg of etodolac per kg of body weight of the patient per day is administered to the patient.

4. The method of claim 3 wherein the etodolac is administered orally to the patient.

5. A method according to claim 1, wherein said therapeutically effective amount of the indole or carbazole compound is sufficient to reduce the level of leukemic lymphocytes in said patient.

6. A method according to claim 1, wherein said indole or carbazole compound is administered in the form of a pharmaceutical composition.

7. A method according to claim 6, wherein said pharmaceutical composition further comprises a pharmaceutically acceptable carrier or diluent.

8. A method for the treatment of B-cell lymphoma in a patient, comprising administering to said patient a therapeutically effective amount of an indole or carbazole derivative of the formula:

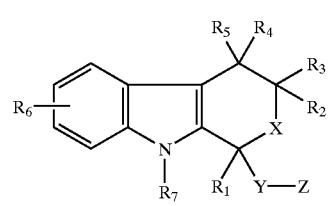

Formula I in which $R_1$ is selected from the group consisting of hydrogen, lower alkyl, lower alkenyl, lower alkynyl, alkoxyloweralkyl, lower cycloalkyl, phenyl, benzyl and 2-thienyl; $R_2$ and $R_3$ are the same or different and are each selected from the group consisting of hydrogen and lower alkyl; $R_4$ and $R_5$ are the same or different and are each selected from the group consisting of hydrogen, lower alkyl, —$NH_2$, —NHCHO, —$NHCONH_2$, =NW, oxo, —OH and —$OCH_3$, wherein W is hydroxy, alkoxy, aryloxy, carboxyalkyloxy, arylamino or alkylsulfonylamino; $R_6$ is selected from the group consisting of hydrogen, lower alkyl, lower alkenyl, lower alkynyl, trifluoromethyl, hydroxy, lower alkoxy, trifluoroloweralkoxy, benzyloxy, araloxy, lower alkanoyloxy, acyl, amino, nitro, cyano, alkylimido, halo, mercapto, loweralkylthio, alkylsulfinyl, alkylsulfonyl, alkylsulfonamido and sulfamoyl; $R_7$ is selected from the group consisting of hydrogen, lower alkyl and lower alkenyl; X is selected from the group consisting of carbon, oxy and thio; Y is selected from the group consisting of carbonyl,

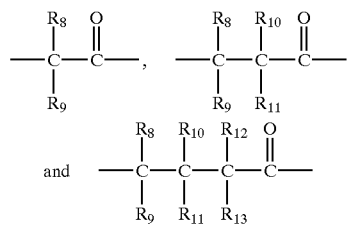

in which each of $R_8$, $R_9$, $R_{10}$, $R_{11}$, $R_{12}$ and $R_{13}$ is hydrogen or lower alkyl; and Z is selected from the group consisting of hydroxy, lower alkoxy, amino, lower alkylamino, di(lower)alkylamino and phenylamino, or a pharmaceutically acceptable salt thereof.

9. The method of claim 8 wherein the indole or carbazole derivative is etodolac.

10. The method of claim 9 wherein about 1.0 mg to 500 mg of etodolac per kg of body weight of the patient per day is administered to the patient.

11. The method of claim 10 wherein the etodolac is administered orally to the patient.

12. A method according to claim 8, wherein said therapeutically effective amount of the indole or carbazole compound is sufficient to reduce the level of leukemic lymphocytes in said patient.

13. A method according to claim 9, wherein said indole or carbazole compound is administered in the form of a pharmaceutical composition.

14. A method according to claim 13, wherein said pharmaceutical composition further comprises a pharmaceutically acceptable carrier or diluent.

* * * * *